United States Patent [19]

Sohma et al.

[11] Patent Number: 4,820,046
[45] Date of Patent: Apr. 11, 1989

[54] SPECTROSCOPE APPARATUS AND REACTION APPARATUS USING THE SAME

[75] Inventors: Kenichi Sohma; Shigeru Azuhata, both of Hitachi; Kiyoshi Narato, Ibaraki; Tooru Inada, Hitachi; Hironobu Kobayashi, Katsuta; Norio Arashi; Hiroshi Miyadera, both of Hitachi, all of Japan

[73] Assignee: Hitachi, Ltd., Tokyo, Japan

[21] Appl. No.: 120,593

[22] Filed: Nov. 12, 1987

[30] Foreign Application Priority Data

Dec. 1, 1986 [JP] Japan .................. 61-286282
Apr. 8, 1987 [JP] Japan .................. 62-84762

[51] Int. Cl.$^4$ .................. G01J 3/18; G01J 3/30; G01J 3/443
[52] U.S. Cl. .................. 356/328; 356/315; 356/316; 356/318; 356/333
[58] Field of Search .................. 356/305, 328, 315–318, 356/331, 332, 333, 334, 300, 301, 394

[56] References Cited

U.S. PATENT DOCUMENTS

| | | | |
|---|---|---|---|
| 4,195,930 | 4/1980 | Delhaye et al. | 356/301 |
| 4,455,087 | 1/1984 | Allemand et al. | 356/333 |
| 4,676,597 | 6/1987 | Cisternino | 350/168 |
| 4,705,396 | 11/1987 | Bergström | 356/334 |

FOREIGN PATENT DOCUMENTS

| | | |
|---|---|---|
| 107890 | 9/1978 | Japan . |
| 94125 | 7/1979 | Japan . |
| 42331 | 4/1981 | Japan . |
| 38464 | 4/1981 | Japan . |
| 151814 | 11/1981 | Japan . |
| 33826 | 2/1983 | Japan . |
| 16966 | 1/1984 | Japan . |
| 61123 | 4/1984 | Japan . |
| 1076393 | 7/1967 | United Kingdom ............ 356/300 |

OTHER PUBLICATIONS

Young, *IBM Technical Disclosure Bulletin*, vol. 8, No. 1, Jun. 1965 pp. 111 and 112.
Alden et al, *Applied Physics*, B29, 1982, pp. 93–97.
Summary Paper of the Lecture in the Spectroscopical Society of Japan, p. 20.

*Primary Examiner*—F. L. Evans
*Attorney, Agent, or Firm*—Antonelli, Terry & Wands

[57] ABSTRACT

A spectroscope apparatus includes means for separating light from an object to be measured into spectral components, means for mixing that part of the spectral components which exists in a desired wavelength range, and means for forming an image of the to-be-measured body of mixed light. The image thus obtained is very useful for observing the state of a combustion flame, the progress of photochemical reaction, the progress of biochemical reaction, a desired tissue in a cell, and the state of a flame for analyzing a solution which contains a metal ion, by flame spectrophotometery, that is, provides accurate information and makes possible a precise control operation.

5 Claims, 12 Drawing Sheets

FIG. 3
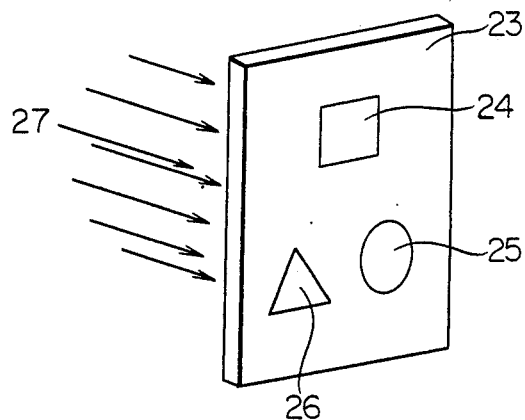
FIG. 4A  FIG. 4B  FIG. 4C
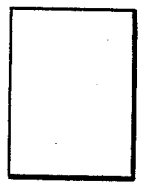 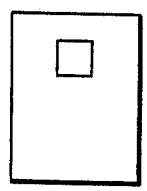 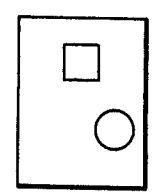
FIG. 4D  FIG. 4E
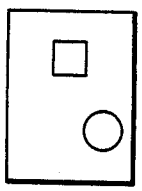 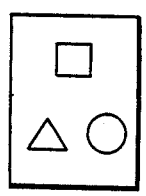

WAVELENGTH ⟶

·OH*  ·CH*  ·C₂*  NO*

SPECTROSCOPE

SPECTROSCOPE APPARATUS AND REACTION APPARATUS USING THE SAME

BACKGROUND OF THE INVENTION

The present invention relates to a spectroscope apparatus, and more particularly to a two-dimensional imaging monochrometer apparatus which can continuously form a plurality of two-dimensional images of a to-be-measured body due to different light components each having a desired spectral width.

Further, the present invention relates to a method of and an apparatus for controlling reaction which is accompanied by light emission due to reaction, discharge or others, and more particularly to a method of and an apparatus for controlling a reactor or instrument containing a light emitting body, on the basis of those images of the light emitting body which are formed by a two-dimensional spectroscope apparatus and are formed of different wavelength component emitted from the light emitting body.

In a conventional apparatus for monitoring or controlling a reactor or instrument containing a substance which emits light on the basis of reaction, discharge and others, a monitor window is provided at the wall of the reactor or instrument, and the inside of the reactor or instrument is observed through the window to control variable quantities contributing to the chemical change of the substance.

For example, in a thermal power station or the like, the state of combustion flames is observed by an industrial television camera through the monitor window, and it is judged on the basis of the above observation and analytical values of exhaust gas whether the state of combustion flames is appropriate or not, to control the quantities of air and fuel so as to obtain optimum flames. Further, an image indicating the brightness distribution in combustion flames is formed on the basis of the observation on combustion flames by the industrial television camera, to be used for monitoring and controlling the combustion flames. For example, a method of monitoring and controlling combustion flames on the basis of the output of a photodetector which receives light from the combustion flames, is disclosed in a Japanese Patent Application JP-A-No. 56-151,814, and a control method using a video signal from a television camera is disclosed in a Japanese Patent Application JP-A-No. 54-94,125. In these methods, however, the output of an industrial television camera due to all the wavelength components emitted from a light emitting substance (namely, light emitting body) is used for monitoring and controlling the light emitting body. That is, the methods fail to use only a desired wavelength component emitted from the light emitting body, for the purpose of monitoring and controlling the above body. In general, the emission spectrum of the light emitting body is based upon active atoms, molecules and radicals which are contained in this body. The information due to each of wavelength components from the light emitting body makes it possible to estimate the state of the body on the level of atom, molecule and radical, and is indispensable for accurate monitoring and control operations.

A method of monitoring or controlling a flame on the basis of the information due to each of wavelength components emitted from the flame, is disclosed in, for example, a Japanese Patent Application JP-A-No. 53-107,890. In this method, the state of a flame is monitored and controlled on the basis of the correlation between the intensities of OH-radical line, $C_2$-radical line and CH-radical line appearing on the emission spectrum of the flame and analytical values of exhaust gas. In the method, however, the intensity of each wavelength component emitted from a point in the flame or the sum of intensities of all wavelength components emitted from the whole region of the flame is used, and thus it is impossible to obtain an image which indicates the distribution of each wavelength component in the flame. Generally speaking, in the reaction generating a light emitting body which always moves, such as a flame, detailed information on the distribution of each wavelength component, that is, the distribution of each chemical species in the flame, teaches the progress of the reaction and the fine structure of the flame, and suggests a position where nitrogen oxide and soot are generated.

Accordingly, a method is required which has not only an advantage of spectrochemical analysis (that is, an advantage that information on each of chemical species in the flame is obtained), but also are advantage of an industrial television camera (that is, an advantage that an image of the flame is formed). There has been known a method, in which an interference filter capable of transmitting only a desired wavelength is provided in front of an industrial television camera. According to this method, an image of a light emitting body can be formed of a desired one of wavelength components emitted from the body. In this method, however, it is necessary to prepare a plurality of interference filters, and it is impossible to change the measuring wavelength continuously, since replacement of interference filter is required for changing the measuring wavelength. Further, an interference filter attenuates light in a great degree, and thus makes it impossible to obtain a clear image by the industrial television camera.

Further, reaction accompanied by light emission occurs in the following apparatuses and methods, that is, a photochemical vapor deposition apparatus (disclosed in a Japanese Patent Application JP-A-No. 56-42,331), a vapor epitaxial growth apparatus (disclosed in a Japanese Patent Application JP-A-No. 58-33,826), a semiconductor fabricating method (disclosed in a Japanese Patent Application JP-A-No. 59-61,123), a method of forming a nitride film (disclosed in a Japanese Patent Application JP-A-No. 56-38,464) and a chemical vapor deposition apparatus (disclosed in a Japanese Patent Application JP-A-No. 59-16,966). In any one of these patent applications, the distribution of each of chemical components of a light emitting body in the body is not measured, and it is not disclosed to monitor and control the light emitting body on the basis of information on the above distribution.

In the simplest conventional method for forming a plurality of images of an object to be measured, of different light components each having a spectral width, optical filters are used, each of which transmits only a light component having a desired spectral width and absorbs or reflects other light components. For example, in a case where a photograph is taken by an ordinary camera in a state that strong ultraviolet rays are present, when an ordinary film is used, blurs in color tone are produced. Accordingly, an ultraviolet cut filter is used, to form an image only of visible light.

Further, in order to thoroughly investigate discharge and combustion phenomena, it is necessary to observe the spatial intensity distribution of a wavelength component peculiar to each of unstable chemical species existing in a discharge plasma or flame such as radicals and active molecules. In this case, only specified wavelength components are measured, and thus optical filters each capable of transmitting one of the specified wavelength components are used. For example, the measurement of unstable chemical species contained in a flame is described in an article (Applied Physics B. Vol. 29, 1982, pages 93 to 97). It is shown in FIG. 1 of this article to use a filter for light from the OH-radical and another filter for light from the $C_2$-radical. However, in a method of forming an image due to light within a specified wavelength range by using a filter, it is required to change the specified wavelength range by the replacement of filter, and hence it is impossible to change a measuring wavelength continuously. Further, a filter attenuates light in a great degree. In the above article, no regard is paid to such problems.

An optical apparatus for forming a plurality of images of an object due to different wavelength components continuously by using a spectroscope, is described on page 20 of the abstracts of the spring meeting of the Spectroscopical Society of Japan held in May, 1985. In this optical apparatus, the measuring wavelength can be continuously varied by rotating a grating included in the spectroscope. Further, in the spectroscope, light reflection is repeated, and no optical filter is used. Thus, light is scarcely attenuated in the spectroscope. In this optical apparatus, however, as is apparent from the description that, since a background having a continuous spectrum is present, a wavelength component which exists in the vicinity of a band head and is not affected by a band spectrum, is used, and an image formed of the wavelength component is corrected by software, there arises the following problem. That is, in a case where light emitted from an object to be measured has a continuous spectrum, the measurement is restricted as above. Further, it is required to correct an image by software, and thus the optical apparatus is complicated in structure.

As mentioned above, in a method of taking desired wavelength components out of light emitted from an object to be measured, by using filters to form a plurality of images of the to-be-measured object, there arise problems that it is impossible to change the taken-out wavelength component continuously, since the wavelength component is changed by the replacement of filter, and that each filter absorbs light, and thus the intensity of the taken-out wavelength component is greatly reduced. Further, in a method of taking out desired wavelength components by using a spectroscope, the taken-out wavelength can be continuously varied, but there arise optical problems that when light incident on the spectroscope has a continuous spectrum within a wavelength range, measurement is restricted as mentioned above or a desired image cannot be formed.

SUMMARY OF THE INVENTION

An object of the present invention is to provide a two-dimensional imaging monochrometer apparatus (spectroscope apparatus) which can form an image of an object to be measured, of a desired wavelength component emitted from the to-be-measured body and moreover can change the desired wavelength component continuously, and which can form the image of the to-be-measured body without being subject to any restriction, even when the light incident on (that is, received by) the spectroscope apparatus has a continuous spectrum in a wavelength range.

Another object of the present invention is to provide a method of and an apparatus for monitoring or controlling reaction accompanied by light emission, by using a two-dimensional imaging monochrometer apparatus which can form an image of an object to be measured, of a desired wavelength component of light emitted from the to-be-measured body and moreover can change the desired wavelength component continuously, and which can form the image of the to-be-measured body without being subject to any restriction, even when the light received by the spectroscope apparatus has a continuous spectrum in a wavelength range.

According to an aspect of the present invention, there is provided a spectroscope apparatus which comprises means for separating light emitted from an object to be measured, into spectral components, means for mixing that part of the spectral components which exists in a desired wavelength range, and means for forming an image of the to-be-measured body, of mixed light. Further, the spectroscope apparatus may be provided with means for making light rays which are formed of the desired spectral part, diverge, and for focusing the divergent light rays to a point before the desired spectral part is mixed.

In more detail, a spectroscope apparatus according to the present invention includes a first spectroscope, a second spectroscope which is coupled with the first spectroscope through an intermediate slit, and drive means for driving the first and second spectroscopes. The first spectroscope includes a collimator system for forming an image of an object to be measured on a light dispersing grating, and includes a light dispersing optical system which is made up of the light dispersing grating and a first optical system for guiding the diffracted light from the light dispersing grating to the intermediate slit. The second spectroscope includes a light mixing optical system which is made up of a light mixing grating and a second optical system for focusing light having passed through the intermediate slit on the light mixing grating, and includes an image formation optical system for forming an image of mixed light from the light mixing optical system. The drive means drives the light dispersing optical system and the light mixing optical system so that these systems are optically symmetrical with respect to the intermediate slit.

A spectroscope apparatus according to the present invention is applicable to light emitted from a flame due to combustion, light due to photochemical reaction which is generated by irradiating a photochemically reactive gas with stimulating light, fluorescence which is emitted from a pigment for staining a desired tissue in a cell, when the pigment is irradiated with predetermined light, and light emitted from a flame at a time a solution containing a metal ion is introduced into the flame. That is, the spectroscope apparatus can separate the above light into spectral components, mix that part of the spectral components which exists in a desired wavelength range, and form an image of mixed light. Thus, a spectroscope apparatus according to the present invention is applicable to a method of monitoring the combustion state of a flame, a method of monitoring photochemical reaction which proceeds in a photochemical reaction apparatus, a method of monitoring biochemical reaction which occurs at a predetermined tissue of a cell, and a method of determining a metal ion by flame spectrochemical analysis.

Thus, according to another aspect to the present invention, there are provided a boiler provided with a spectroscope apparatus which receives light from a flame generated in the furnace of the boiler; a gas turbine made up of a compressor for compressing air, a combustor for burning fuel with the aid of compressed air, a turbine driven by a combustion gas, and a spectroscope apparatus which receives light from a flame generated in the combustor; a photochemical reaction apparatus for proceeding photochemical reaction by irradiating photochemically reactive gas with stimulating light which reaction apparatus is provided with a spectroscope apparatus receiving light due to the photochemical reaction; a biochemical reaction apparatus for irradiating a pigment having stained a desired tissue in a cell, with light to generate fluorescence from the pigment which reaction apparatus is provided with a spectroscope apparatus receiving the fluorescence; and an analytical apparatus for determining a metal ion in a solution by flame spectrophotometry which analytical apparatus is provided with a spectroscope apparatus receiving light from a flame. Each of the above spectroscope apparatus includes means for separating incident light into spectral components, means for mixing that part of the spectral components which exists in a wavelength range, and means for forming an image of mixed light.

Incidentally, the above-mentioned photochemical reaction apparatus includes a photochemical vapor deposition apparatus, a vapor phase epitaxial growth apparatus, and a chemical deposition apparatus. Further, the stimulating light is selected from visible light, infrared rays, ultraviolet rays and a laser beam.

Further, according to a further aspect of the present invention, there is provided a method of controlling the reaction accompanied by light emission, in which light from a light emitting body is separated into spectral components, that part of the spectral components which exists in a desired wavelength range is mixed to form an image of the light emitting body of mixed light, a plurality of images of the light emitting body are formed in accordance with a plurality of desired wavelength ranges, the images thus obtained are compared with previously-prepared reference images, and variable quantities concerning the state of the light emitting body are controlled so that the images agree with the reference images.

In the above control method, it is preferable that a region where one of chemical species contained in the light emitting body is present, is increased in area and a region where another chemical species is present, is reduced, when the supply quantity of one of raw materials of the light emitting body is changed. For example, it is preferable that the light emitting body is a combustion gas, and one and another chemical species are $C_2$-radical and NO-radical, respectively.

The desired wavelength range is selected from the whole spectral range of light emitted from the light emitting body, and it is preferable that the desired wavelength range is a wavelength range from a wavelength longer than a specified wavelength by 2.5 nm to a wavelength shorter than the specified wavelength by 2.5 nm.

Further, according to still another aspect of the present invention, there is provided an apparatus for controlling the reaction accompanied by light emission which apparatus includes a reaction apparatus for forming a light emitting body therein, an optical guide for forming an optical path for light emitted from the light emitting body, two-dimensional imaging monochrometer apparatus for separating light from the optical guide into spectral components, a monitor for displaying a plurality of images which are formed of light components having different wavelength ranges, a memory for storing a plurality of reference images, and a controller for displaying each of the images and a corresponding one of the reference images at the same time to control variable quantities concerning the state of the light emitting body so that the images agrees with the reference image. The two-dimensional imaging monochrometer apparatus includes a first spectroscope, a second spectroscope which is coupled with the first spectroscope through an intermediate slit, and drive means for driving the first and second spectroscopes. The first spectroscope includes a collimator system for focusing the light to be measured on a light dispersing grating, and includes a light dispersing optical system which is made up of the light dispersing grating and a first optical system for leading the diffracted light from the light dispersing grating to the intermediate slit. The second spectroscope includes a light mixing optical system which is made up of a light mixing grating and a second optical system for focusing light having passed through the intermediate slit, on the light mixing grating, and includes an image formation optical system for forming an image of the mixed light from the light mixing optical system. The drive means drives the light dispersing optical system and the light mixing optical system so that these systems are optically symmetrical with respect to the intermediate slit.

The above apparatus for controlling the reaction accompanied by light emission can control the state of the light emitting body accurately, provided that the image formation optical system of the second spectroscope is provided with a light amplifying element, the width of the intermediate slit is variable, the rotational angle of each of the light dispersing grating and the light mixing grating can be varied continuously, while maintaining a state that these gratings are optically symmetrical with respect to the intermediate slit, the optical guide includes a lens capable of transmitting light within a wavelength range from an ultraviolet region to an infrared region, and the light intensity distribution at an image formed of mixed light can be expressed in colors.

According to the above apparatus for controlling the reaction accompanied by light emission, light is drawn from a reactor or instrument in which the reaction or phenomenon accompanied by light emission proceeds, an image due to part of the spectral components of the drawn light is continuously formed by the two-dimensional imaging monochrometer apparatus, and the chemical species distribution in the light emitting body is monitored with the aid of the images, or the reaction or phenomenon is controlled so that the chemical species distribution is optimum. That is, the state of the light emitting body is estimated on the level of chemical species such as an atom, a molecule and a radical, and thus can be accurately monitored or controlled. Further, information on the distribution of each of chemical species such as an atom, a molecule and a radical, can be obtained, and thus generation and extinction processes in reaction can be observed. That is, the progress of the reaction can be estimated, and the reaction can be monitored or controlled more accurately.

As mentioned above, in an apparatus for controlling the reaction accompanied by light emission according to the present invention, light from an object to be measured is separated into spectral components, that part of the spectral components which exists in a desired wavelength range is mixed, and a very clear image of the to-be-measured object is formed of mixed light. Such an image provides information useful for controlling the combustion state of a fuel generated in a furnace, the progress of photochemical reaction and the progress of biochemical reaction, and useful for the observation on a cellular texture and the flame spectrophotometric analysis of a metal ion contained in a solution. That is, the above image makes possible a precise control operation, and provides accurate information.

In a two-dimensional imaging monochrometer apparatus according to the present invention, incident light passes through the collimator system and the light dispersing optical system of the first spectroscope, and then only part of the spectral components of the incident light reaches the intermediate slit. Thus, the first spectroscope functions as a light dispersing element. The intermediate slit passes a desired range of the wavelength of the light. The spectral part from the intermediate slit passes through the light mixing optical system and the image formation optical system of the second spectroscope, to form an image of mixed light. Thus, the second spectroscope functions as a light mixing element. By driving the light dispersing optical system of the first spectroscope and the light mixing optical system of the second spectroscope so that these systems are optically symmetrical with respect to the intermediate slit, the wavelength of mixed light used for forming the image can be continuously varied.

As mentioned above, a two-dimensional imaging monochrometer apparatus according to the present invention can continuously form a plurality of images due to part of the spectral components of incident light. Thus, the spectroscope apparatus can clearly shows the chemical species distribution in a light emitting body which is generated in a reactor or instrument, and makes it possible to monitor the light emitting body or control variable quantities concerning the generation of the light emitting body so that the optimum distribution of a chemical species in the light emitting body is achieved.

BRIEF DESCRIPTION OF THE DRAWINGS

FIG. 3 is a schematic diagram showing a test plate which is used for measuring the wavelength resolving power and spatial resolving power of the embodiment of FIG. 1.

FIGS. 4A to 4E are schematic diagrams showing the results of measurements of the wavelength resolving power and spatial resolving power of the embodiment of FIG. 1.

DESCRIPTION OF THE PREFERRED EMBODIMENTS

EXAMPLE I

Figure 5:
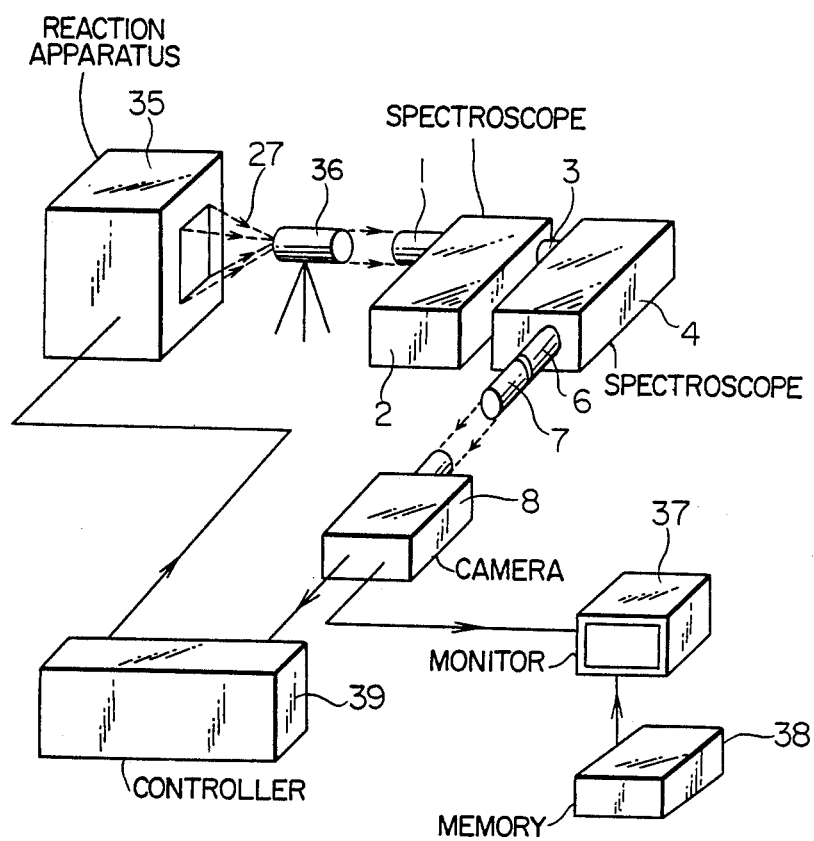
FIG. 5 is a schematic diagram showing an embodiment of a monitor/control apparatus according to the present invention.

FIG. 5 shows an embodiment of a monitor/control apparatus according to the present invention. Referring to FIG. 5, the present embodiment includes an optical guide 36 receiving light from a light emitting body which is formed in a reaction apparatus 35 as the result of reaction (or a phenomenon) accompanied by light emission, a two-dimensional imaging monochrometer apparatus for successively outputting a plurality of images formed of desired ones of wavelength components of incident light, a camera 8 for forming an image which shows the reaction product (namely, chemical species) distribution in the light emitting body, on the basis of the output images from the spectroscope apparatus, a monitor 37, a memory 38 for previously storing reference images, and a controller 39 for controlling variable quantities concerning the generation of the light emitting body on the basis of the comparison of the image from the camera 8 with a reference image from the memory 38 so that optimum reaction-product distribution in the light emitting body is obtained. The reference image may be displayed on the display screen of the monitor 37 together with the image from the camera 8, or may be displayed by another monitor (not shown). The reference image is used as the standard of the image obtained from the camera 8, and the reaction product distribution and a light and shade pattern in the image are compared with those in the reference image. Accordingly, a plurality of reference images corresponding to a plurality of images which are formed of different wavelength components, are stored in the memory 38. In a case where only a monitoring operation is performed, the memory 38 and the controller 39 may be omitted from the present embodiment.

The two-dimensional imaging monochrometer apparatus includes a first spectroscope 2 which is provided with a condenser lens 1 for collecting light rays from the optical guide 36, an intermediate slit 3, and a second spectroscope 4. A relay lens group 6 and a focusing lens group 7 act as a focusing optical system for the second spectroscope 4. In other words, the lens groups 6 and 7 forms an image due to that part of the spectral components of light incident on the condenser lens 1 which exists in a desired wavelength range, on the light receiving surface of the camera, without producing astigmatism chromatic aberration.

Figure 6:
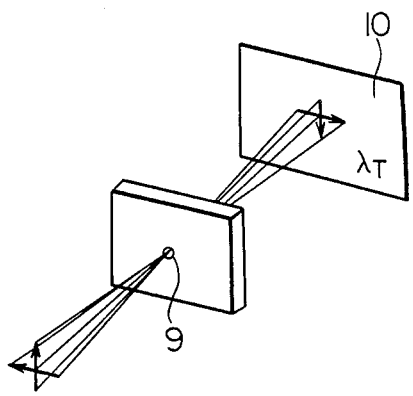
FIG. 6 is a schematic diagram for explaining the optical principle of a pinhole camera.
Figure 7:
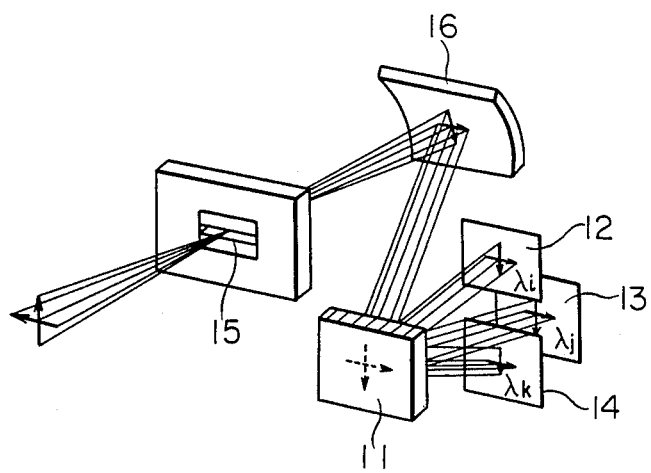
FIG. 7 is a schematic diagram for explaining the optical principle of image formation which is carried out by a spectroscope apparatus according to the present invention.

First, the operation principle of the two-dimensional imaging monochrometer apparatus capable of forming an image of a light emitting body to be measured, of a desired wavelength component, will be explained while being compared with that of a pinhole camera, with reference to FIGS. 6 and 7. Referring to FIG. 6 which shows the operation principle of a pinhole camera, a pinhole 9 acts as the point source of light rays for forming an image, and the upper and lower parts of light rays passing through the pinhole 9 are replaced with each other at the pinhole 9. Further, the left and right parts of the light rays are replaced with each other at the pinhole 9. Then, the image is formed on a film 10. That is, all wavelength components $\lambda_T$ contains in incident light contribute to the formation of the image. In the two-dimensional imaging monochrometer apparatus, a grating 11 which diffracts different wavelength components in different directions, is disposed in place of the film 10. Accordingly, as shown in FIG. 7, images due to wavelength components $\lambda_i$, $\lambda_j$ and $\lambda_k$ are formed on screens 12, 13 and 14, respectively. In FIG. 7, a slit 15 performs a function corresponding to that of the pinhole 9. That is, at the slit 15, the upper and lower parts of light rays are replaced with each other, and the left and right parts of the light rays are replaced with each other. As shown in FIG. 7, light rays having passed through the slit 15 form a divergent light beam, which is converted by a concave mirror 16 into parallel light rays. The parallel light rays thus obtained are diffracted by the grating 11, that is, different wavelength components are reflected from the grating 11 in different directions.

Figure 8:
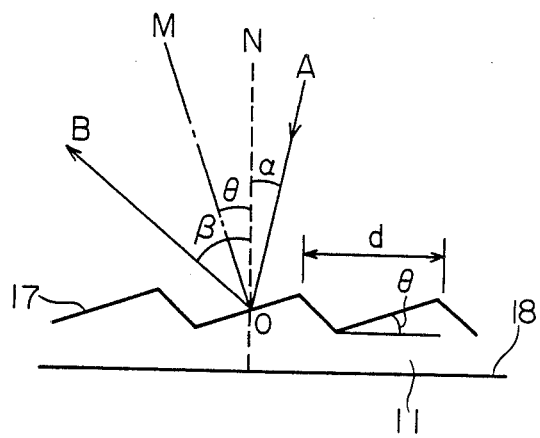
FIG. 8 is a schematic diagram showing a cross section of an echelette plane grating which is usable in a spectroscope apparatus according to the present invention.

Now, an echelette plane grating used in a spectroscope apparatus according to the present invention will be explained, with reference to FIG. 8. As shown in FIG. 8, the cross section of one main surface of an echellette plane grating 11 has the form of saw-teeth parallel to two planes. An angle $\theta$ between a groove surface 17 and a grating plane 18 is called blaze angle. Let us express the distance between adjacent grooves (namely, grating constant), an incident angle between incident light OA and a normal ON to the grating plane 18, and an angle between reflected light OB and the normal ON, by d, $\alpha$ and $\beta$, respectively. When an optical path difference between light beams diffracted from adjacent grooves is equal to an integer multiple of a wavelength $\lambda$, the light beams are in phase. That is, constructive interference takes place between the light beams, when the factors d, $\alpha$, $\beta$ and $\lambda$ satisfy the following equation:

$$m\lambda = d (\sin \alpha + \sin \beta), \quad (1)$$
when m=0, +1, +2, and so on   (1)

Incidentally, m indicates the spectral orders.

For example, let us consider the diffracted light of the first order indicated by m=1. When the incident light AO having a wavelength $\lambda$ makes an angle $\alpha$ with the normal ON to the grating plane 18, the light OB diffracted from the groove surface 17 having a grating constant d makes an angle $\beta$ with the normal ON.

Figure 9:
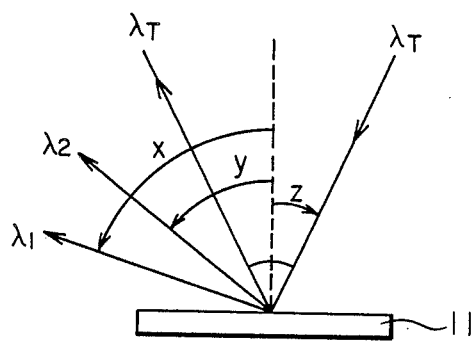
FIG. 9 is a schematic diagram for explaining light reflection from an echelette plane grating.

Referring to FIG. 9, when light $\lambda_T$ incident on the echellette plane grating has two wave components $\lambda_1$ and $\lambda_2$, an angle x between the diffracted wavelength component $\lambda_1$ and a normal to the grating plane 18 and an angle y between the diffracted wavelength component $\lambda_2$ and the normal, can be calculated from the equation (1). It is to be noted that when the wavelength $\lambda_1$ is longer than the wavelength $\lambda_2$, the angle x is greater than the angle y.

Figure 10:
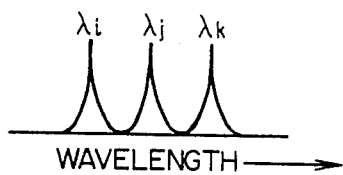
FIG. 10 shows an example of the spectrum of incident light.
Figure 11:
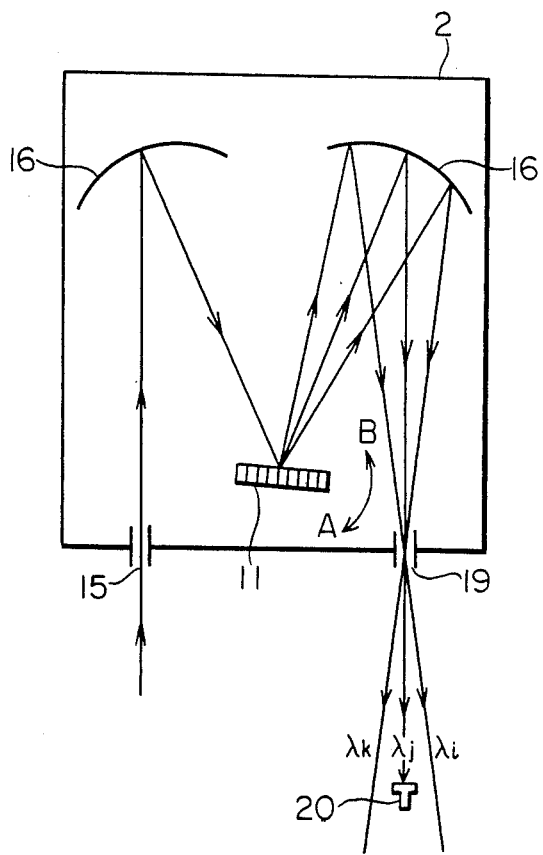
FIG. 11 is a schematic diagram for explaining the optical path formed in a spectroscope.
Figure 12:
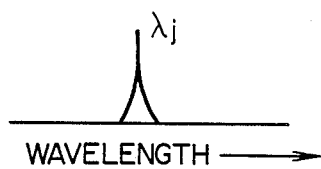
FIG. 12 shows an example of the spectrum of light emerging from the spectroscope of FIG. 11.

The above fact holds for a case where incident light is formed of three or more spectral lines, that for a case where the incident light is formed of a plurality of spectral lines each having a very small spectral width, or a difference in wavelength between adjacent spectral lines of incident light is greater than the resolving power of the spectroscope 2. Accordingly, when incident light has three wavelength components $\lambda_i$, $\lambda_j$ and $\lambda_k$ as shown in FIG. 10, three images due to the wavelength components $\lambda_i$, $\lambda_j$ and $\lambda_k$ are formed on the screens 12, 13 and 14, respectively. In an ordinary case where the imaging surface of the camera 8 is used as the screen, that is, only a single screen is used, three images are successively projected on the screen by rotating the grating 11. In a spectroscope or the like, as shown in FIG. 11, a detector 20 for detecting light from an exit slit 19 corresponds to the screen, and only a spectral component incident on the exit slit 20 at right angles is detected by the detector 20. That is, when light $\lambda_T$ incident on the spectroscope contains three spectral lines $\lambda_i$, $\lambda_j$ and $\lambda_k$ as shown in FIG. 10, the light $\lambda_T$ is separated by the grating 11 into three wavelength components $\lambda_i$, $\lambda_j$ and $\lambda_k$, which are focused on the exit slit 19 by a concave mirror 16. In FIG. 11, the wavelength component $\lambda_j$ is incident on the exit slit 20 at right angles, and thus an image formed of only the wavelength component $\lambda_j$ is detected by the detector 20. FIG. 12 shows the spectrum of the detected image. In order to detect the wavelength component $\lambda_i$, the grating 11 is rotated in a direction A so that the wavelength component $\lambda_i$ is incident on the exit slit 20 at right angles. Similarly, in order to detect the wavelength component $\lambda_k$, the grating 11 is rotated in a direction B.

Figure 14:
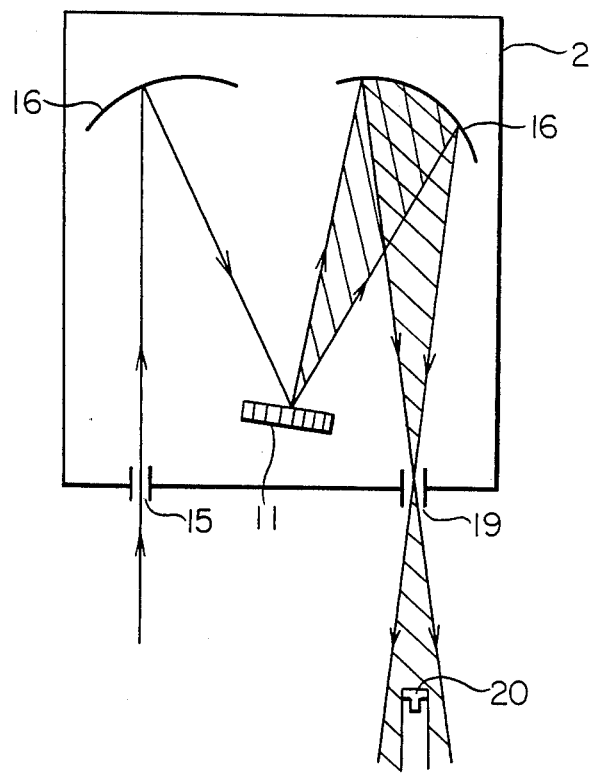
FIG. 14 is a schematic diagram which shows an optical path in the spectroscope of FIG. 11 corresponding to the incident light of FIG. 13.
Figure 15:
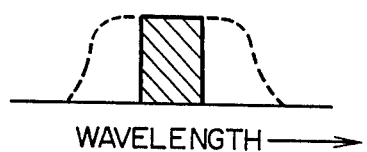
FIG. 15 shows the spectrum of outgoing light corresponding to the incident light of FIG. 13.

In the above, explanation has been made of a case where the incident light $\lambda_T$ is composed of discrete spectral lines. In a case where the incident light $\lambda_T$ has a band spectrum shown in FIG. 13, a light component detected by the detector 20 has a spectral width as shown in FIG. 14. That is, the detected light component has a spectrum shown in FIG. 15. In other words, a correct image is not formed on each of the screens 12, 13 and 14 of FIG. 7, but a beltlike image spread or blurred in a longitudinal direction is formed on each screen (it is to be noted that the length of the image in a transverse direction is determined by the length of the slit and hence the image is not blurred in the transverse direction). That is, in a case where the incident light has a band spectrum as shown in FIG. 13, it is impossible to form a plurality of correct images by using a single spectroscope.

Figure 1:
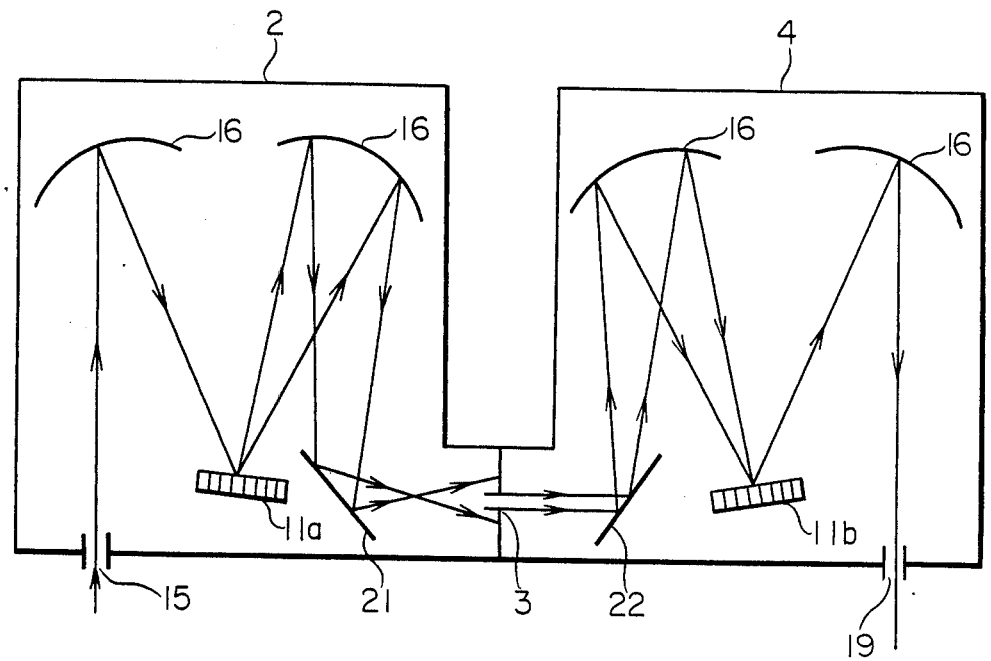
FIG. 1 is a schematic diagram showing an optical path in an embodiment of a spectroscope apparatus according to the present invention.
Figure 13:
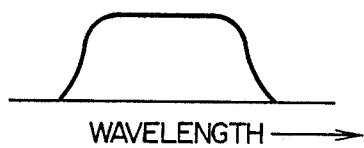
FIG. 13 shows an example of the spectrum of light incident on the spectroscope of FIG. 11.

FIG. 1 shows an optical system according to the present invention capable of forming an image which is not blurred, even in a case where incident light has a band spectrum as shown in FIG. 13 and outgoing light from the exit slit 19 has a continuous spectrum in a wavelength range. Needless to say, the above optical system is used in the embodiment of FIG. 5. Referring to FIG. 1, the first spectroscope 2 has the same function as the spectroscope shown in FIGS. 11 and 14. Accordingly, a grating 11a in the spectroscope 2 functions as a light dispersing element. That is, the light dispersing grating 11a diffracts wavelength components of incident light in different directions. If the incident light on and the diffracted light from the grating 11a are propagated in reverse directions, the grating will function as a light mixing element. In more detail, referring back to FIG. 9, when the wavelength component $\lambda_1$ impinges on the grating 11 in a direction which makes an angle x with a normal to the grating plane, and the wavelength component $\lambda_2$ impinges on the grating 11 in a direction which makes an angle y with the normal, the light $\lambda_T$ composed of the wavelength components $\lambda_1$ and $\lambda_2$ is reflected from the grating 11 in a direction which makes an angle z with the normal. Thus, the grating 11 can act as a light mixing element. The second spectroscope 4 of FIG. 1 is disposed so as to perform a light mixing function. That is, the optical elements of the first spectroscope 2 and those of the second spectroscope 4 are made optically symmetrical with respect to the intermediate slit 3. In more detail, a light dispersing optical system of the first spectroscope 2 is made up of the light dispersing grating 11a and a first optical system including a concave mirror 16 and a plane mirror 21 for guiding the dispersed light from the grating 11a to the intermediate slit 3. A light mixing optical system of the second spectroscope 4 is made up of a light mixing grating 11b and a second optical system including a plane mirror 22 and a concave mirror 16 for focusing the dispersed light on the grating 11b. Drive means (not shown) drives the light dispersing optical system and the light mixing optical system so that these optical systems are optically symmetrical with respect to the intermediate slit 3. Thus, the outgoing light from the exit slit 19 of the second spectroscope 4 is not dispersed. When a screen is disposed in front of the exit slit 19, the outgoing light can form an image which is not blurred, on the screen. The condenser lens 1 of FIG. 5 and a concave mirror 16 confronting an entrance slit 15 make up a collimator. A concave mirror 16 confronting the exit slit 19, the relay lens group 6 and the focusing lens group 7 make up an image formation optical system. It is determined by the rotational angle of the gratings 11a and 11b what part of the spectrum of incident light passes through the exit slit 19, and the wavelength range used for forming the outgoing light from the exit slit 19 is determined by the width of the intermediate slit 3.

Hence, it is desirable to make variable the width of the intermediate slit 3.

Figure 2:
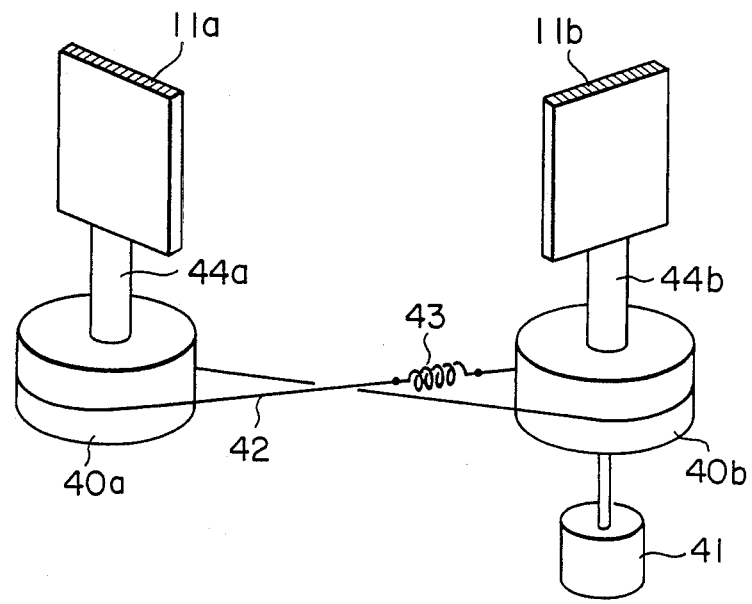
FIG. 2 is a schematic diagram showing an embodiment of the arrangement for driving gratings.

The optical system is so arranged that the incident light is focused on the light dispersing grating 11a is the first spectroscope 2. FIG. 2 shows the schematic diagram of one embodiment in which the light dispersing grating 11a in the first spectroscope 2 and the light mixing grating 11b in the second spectroscope 4 are driven so as to be optically symmetrical with a center of symmetry about the intermediate slit 3. In this embodiment, pulley 40a is connected to grating 11a by shaft 44a and light mixing grating 11b is connected to pulley 40b by shaft 44b. The pulley 40b is driven by motor 41. The pulley 40a is communicated with the pulley 40b by wire 42 which is crossed and includes tension spring 43 connected between the ends of wire 42. The wire 42 and the tension spring 43 may be made of high strength steel like a piano wire. In above system, the gratings 11a and 11b are arranged in optical symmetry with each other about the intermediate slit 3 and the light dispersing grating 11a and the light mixing grating are driven by the motor 41 so as to be optically symmetrical about the intermediate slit 3.

Now, explanation will be made of experiments on the wavelength resolving power and the spatial resolving power (namely, the resolution of image) of the two-dimensional imaging monochrometer apparatus according to the present invention. Referring to FIG. 3, square, circular and trianglar through holes are formed in a black board 23, and filled with color filters. That is, a color filter 24 capable of transmitting wavelengths more than 390 nm is inserted in the square through hole, a color filter 25 capable of transmitting wavelengths more than 460 nm is inserted in the circular through hole, and a color filter 26 capable of transmitting wavelengths more than 620 nm is inserted in the triangular through hole. The black board 23 is illuminated with white light (namely, sunlight) 27 as shown in FIG. 3, and light having passed through the color filters 24, 25 and 26 is led to the spectroscopes 2 and 4 through the condensor lens 1 to form images of the color filters. The gratings 11a and 11b are rotated so as to be optically symmetrical with respect to the intermediate slit 3, to project a plurality of images on the light receiving surface of the camera 8, and the images are observed. The results of the experiments are shown in FIGS. 4A to 4E. In a case where the gratings 11a and 11b were rotated so that light having a wavelength of 300 nm passed through the exit slit 19, no image was formed as shown in FIG. 4A, since the filters 24, 25 and 26 were unable to transmit the above light. In a case where the gratings were set so that light having a wavelength of 400 nm passed through the exit slit 19, only an image of the square through hole was formed as shown in FIG. 4B, since the filter 24 was able to transmit the light. In a case where the gratings were set so as to send out light having a wavelength of 500 nm, images of the square and circular through holes were obtained as shown in FIG. 4C, since the filters 24 and 25 were able to transmit the light. In a case where the gratings were set so as to send out light having a wavelength of 600 nm, the same images as shown in FIG. 4C were obtained as shown in FIG. 4D, since the filter 26 was unable to transmit the light. Further, in a case where the gratings were set so as to send out light having a wavelength of 700 nm, images of the square, circular and triangular through holes were formed as shown in FIG. 4E, since all of the filters 24, 25 and 26 were able to transmit the light.

FIGS. 4A to 4E show that the two-dimensional imaging monochrometer apparatus has favorable wavelength resolving power, and images formed by the spectroscope apparatus in excellent in resolution.

In the above experiments, the black board 23 having dimensions of 150 mm×100 mm was used. However, the size of an object to be measured can be varied by changing the condenser lens 1. In the above experiments, a wavelength range from 300 nm to 700 nm was used. However, the measuring wavelength range is dependent upon the characteristics of the gratings 11a and 11b. The present embodiment can use ultraviolet rays, visible rays and infrared rays. Further, it was confirmed by experments that the wavelength range of that spectral portion of incident light which contributed to the formation of one image could be increased to about 70 Å by setting the width of the intermediate slit 3 appropriately.

As mentioned above, in the present embodiment, light rays from an object to be measured, are collected by the condenser lens, and then separated by the first spectroscope into spectral components. A desired part of the spectral components is mixed by the second spectroscope which is disposed so that the first and second spectroscopes are optically symmetric with respect to the intermediate slit, and an image due to mixed light is formed on the light receiving surface of the camera without having astigmatism and chromatic aberration. Accordingly, even in a case where light from the to-be-measured body has a continuous spectrum, a desired spectral part can be continuously taken out of the continuous spectrum by the first spectroscope, and the taken-out spectral part is converted by the second spectroscope into mixed light. Thus, images can be continuously detected without being subjected to any restriction.

EXAMPLE II

Figure 16:
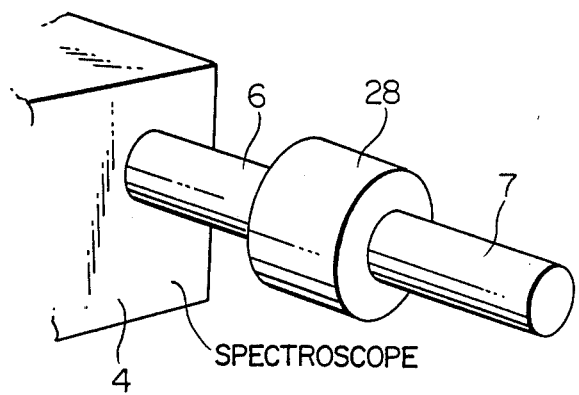
FIG. 16 is a perspective view showing a main part of another embodiment of a monitor/control apparatus according to the present invention.

The outgoing light from the exit slit 19 is a spectral part of incident light. Accordingly, in some cases, the outgoing light has a very weak intensity, and cannot form a clear image. Another embodiment of a monitor/-control apparatus according to the present invention can solve the above problem. The present embodiment is different from the embodiment of FIG. 5 only in that, as shown in FIG. 16, a two-dimensional amplifying element 28 for amplifying a faint image is interposed between the relay lens group 6 and the focusing lens group 7.

Figure 17:
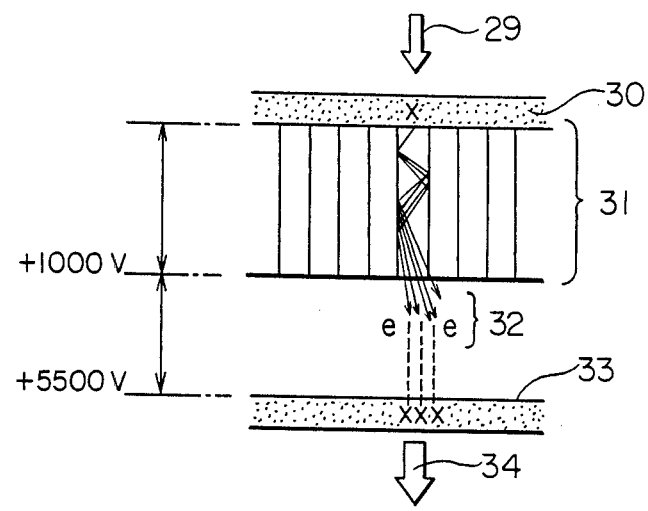
FIG. 17 is a schematic diagram for explaining the optical principle of the light amplifying element of FIG. 16.

The operation principle of the amplifying element 28 will be explained below, with reference to FIG. 17. It is impossible to multiply a photon 29 itself. Hence, the photon 29 is converted into electron, which is converted into a multiplicity of secondary electrons. Then, the secondary electrons are converted into photon. In more detail, the photon 29 is converted by a photocathode surface 30 into a primary electron, which is multiplied to one thousand or more secondary electrons by a secondary electron multiplier 31. The multiplier 31 utilizes a phenomenon that when a metal wall is bombarded with an electron, a plurality of secondary electrons are emitted from the metal wall, and such electron mutliplication is repeated a plurality of times in the multiplier 31, as shown in FIG. 17. The secondary electron mutlipler 31 has a length of about 300 μm, and a voltage of about 1,000 V is applied between both ends of the multiplier 31 so that electrons are accelerated in a direction from the photocathode toward an anode. Secondary electrons 32 emerging from the multiplier 31 are accelerated by an acceleration voltage of 4,500 V, and then bombard a fluorescent screen 33, to be converted into photons 34. Thus, very weak light is converted into strong light whose intensity is more than one thousand times greater than the intensity of the very weak light.

EXAMPLE III

Figure 18:
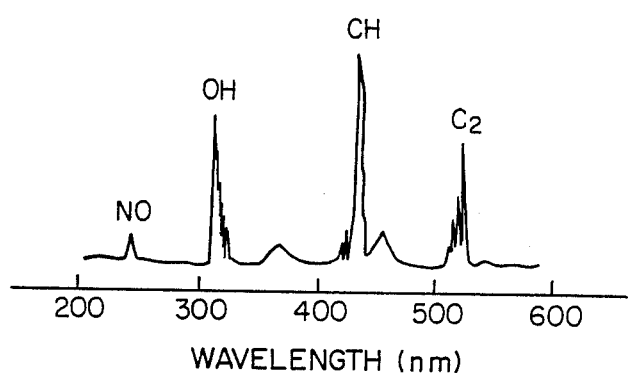
FIG. 18 shows an example of the emission spectrum of flame.
Figure 19:
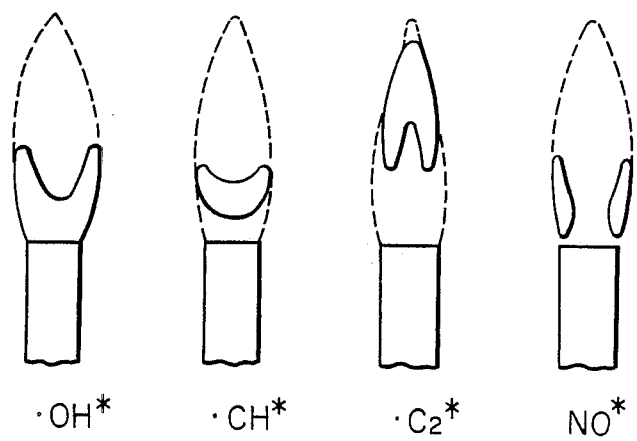
FIG. 19 is a schematic diagram showing radical distribution in a flame on the basis of those images of the flame which are obtained by the present invention.
Figure 20:
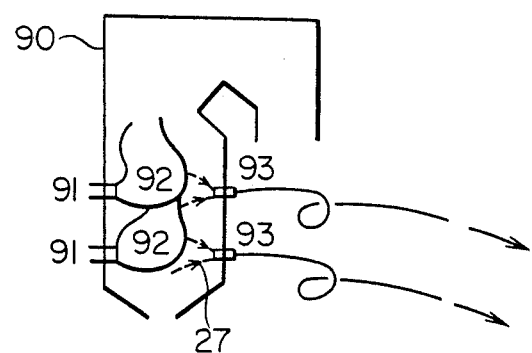
FIG. 20 shows how light emitted from flames is led to a monitor/control apparatus according to the present invention.

A burner made up of a fuel supply nozzle and an air supply nozzle disposed outside of the fuel supply nozzle coaxially therewith was used for making a diffused flame from propane and air, and an emission spectrochemical analysis was made for the flame. FIG. 18 shows the emission spectrum of the flame. It was known from FIG. 18 that OH—, CH—, $C_2$— and NO-radicals were present in the flame. Thus, the radical distribution in the flame was monitored by the embodiment of FIG. 5. That is, the burner was used as the reaction apparatus 35, and an image of the flame was displayed on the display screen of the monitor 37. Thus, the distribution of each radical in the flame was displayed as shown in FIG. 19. It was known that when the supply of air was reduced, a $C_2$-radical existing region was enlarged and soot was generated. Further, it was known that when the supply of air was increased, an NO-radical existing region was enlarged and the amount of resulting nitrogen oxide was increased. However, OH— and CH-radicals were scarcely affected by a change in air supply. By utilizing the above facts, it is possible to maintain an optimum combustion state, in which soot is not generated and a very small amount of nitrogen oxide is produced. The control operation will be explained below in more detail, with reference to FIG. 20. Referring to FIG. 20, burners 91 provided in a furnace 90 generate flames 92, and light emitted from the flames 92 is introduced into image fibers 93. The output light from the fibers 93 is recieved by the condenser lens 1 of FIG. 5. Then the gratings 11a and 11b are set so as to select a wavelength component due to a desired radical from the spectrum of the flames, the distribution of the desired radical in the flames can be monitored. By process variables concerning the state of flames such as the pressure and flow rate of each of supplied fuel and supplied air on the basis of the comparison of an image indicating the distribution of the desired radical with a corresponding reference image, a favorable flame can be maintained. Further, when the controller 39 is operated, the air supply and fuel supply can be controlled accurately and instantaneously on the basis of information from the camera 8. According to the present invention, the state of a flame is controlled on the basis of the reaction product (namely, chemical species) distribution in the flame, and thus the flame can be controlled reliably.

EXAMPLE IV

Figure 21:
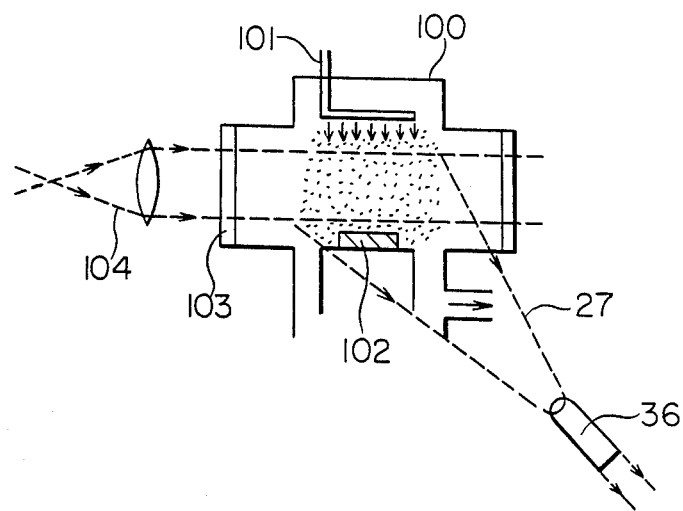
FIG. 21 shows that light from a photochemical reaction apparatus is received by a monitor/control apparatus according to the present invention.
Figure 22:
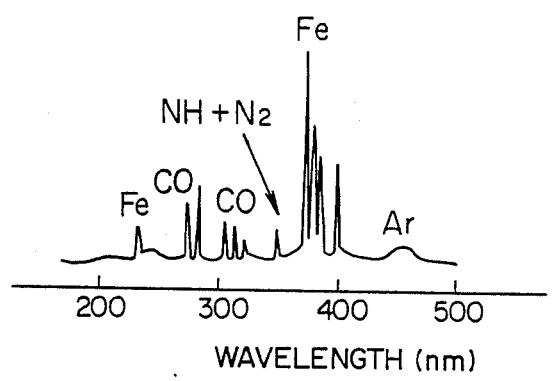
FIG. 22 shows an example of the spectrum of light emission due to photochemical reaction.

In a photochemical vapor deposition apparatus, a plasma chemical vapor deposition apparatus and others, as shown in FIG. 21, a raw material is introduced from a nozzle 101 into a vacuum reactor 100, and light 104 having a wavelength necessary for photochemical reaction illuminates the raw material through a light transmitting window 103, to deposit a solid substance on a substrate 102. By using $Fe(CO)_3$ and $NH_3$ as the raw material, a thin iron nitride film was deposited on the substrate 102. This reaction was accompanied by light emission. An emission spectral analysis was made for the emitted light, to obtain a spectrum shown in FIG. 22. Thus, it was confirmed that chemical species such as Fe, CO and $NH+H_2$ were present. Needless to say, it is desirable that each of the chemical species is distributed in the reactor 100 in an optimum state. Accordingly, the embodiment of FIG. 5 was applied to the light generated by the photochemical reaction. That is, the supply of raw material, the intensity of the illumination light 104, an exposure time and others were controlled by the controller 39 on the basis of the comparison of an image indicating the present distribution of a desired chemical species with a reference image indicating the optimum distribution of the chemical species. The optimum distribution of the chemical species was determined on the basis of the properties of the thin iron nitride film deposited, and the properties of the iron nitride film were measured by appropriate methods.

EXAMPLE V

Figure 23:
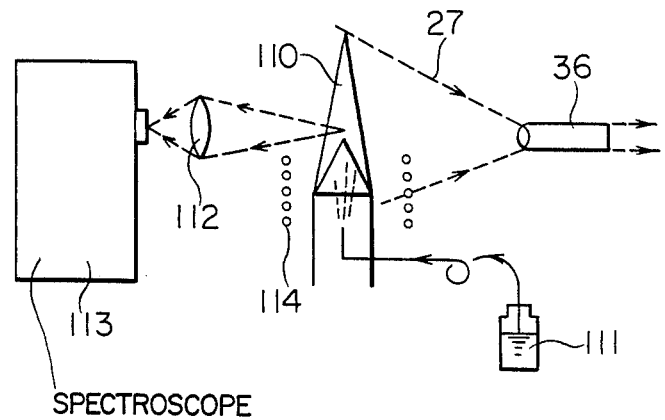
FIG. 23 is a schematic diagram showing that the present invention is applicable to the determination of a sampling position for emission spectrochemical analysis.

In flame spectrochemical analysis, as shown in FIG. 23, a flame 110 is strongly activated by a magnetic field due to an induction coil 114, and a solution containing a metal ion and other is ejected from a nozzle into the flame 110. At this time, light from the metal ion and others is led to a spectroscope 113 through a condenser lens 112, to obtain an emission spectrum, thereby determining the metal ion and others quantitatively. In the above analytical method, the condenser lens 112 is disposed so that light from that portion of the flame 110 where the light emission from the metal ion is strongest, is incident on the entrance slit of the spectroscope 113. The light emission from a metal ion is based upon the following process. That is, a metal ion in the solution is vaporized in the flame 110, and then excited to emit light. Accordingly, the position where the light emission from the metal ion is strongest, varies with the kind of metal ion. In the prior art, it takes a lot of time to find the above position. When the embodiment of FIG. 5 is used, an image due to a wavelength component emitted from the metal ion can be formed and monitored. Accordingly, the position where the light emission from the metal ion is strongest, can be instantaneously found, and the condenser lens 112 and the spectroscope 113 are set so that the entrance slit receives light from the above position.

EXAMPLE VI

In order to observe a desired tissue in a cell, a pigment capable of staining the tissue efficiently is added to the cell, and the tissue is observed with the aid of fluorescence emitted from the pigment. Accordingly, in a case where it is desired to observe a plurality of tissues in a cell, it is necessary to prepare samples, the number of which is equal to the number of tissues.

Figure 24:
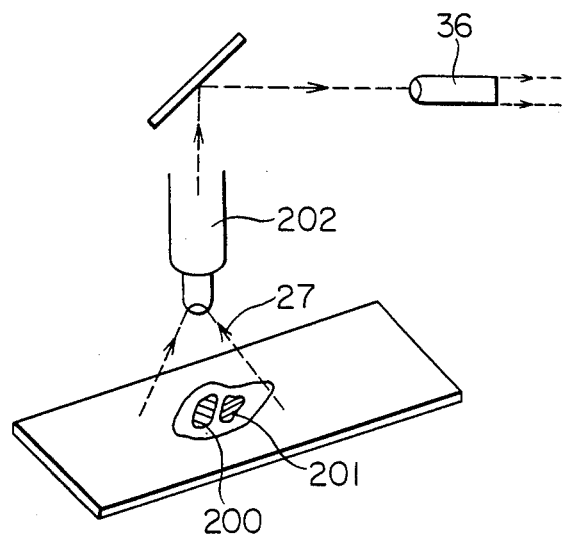
FIG. 24 is a schematic diagram showing an example of the observation on a desired tissue of a cell, according to the present invention.

However, according to the present invention, as shown in FIG. 24, two tissues 200 and 201 in one sample can be observed. That is, a pigment capable of staining the tissue 200 efficiently and another pigment capable of staining the tissue 201 efficiently are added to the sample, and light emitted from the sample is led to the optical guide 36 through an objective lens group 202. The output wavelength of the two-dimensional imaging monochrometer apparatus is first set to the fluorescence from the pigment used for the tissue 200, and then set to the fluorescence from the pigment used for the tissue 201. Thus, respective images of the tissues 200 and 201 due to fluorescence are successively obtained. That is, a plurality of tissues in one sample can be observed. However, it is necessary to appropriately choose the pigments so that the wavelength of fluorescence emitted from a pigment which is used to stain the tissue 200, is different from the wavelength of fluorescence emitted from another pigment which is used to stain the tissue 201.

We claim:
1. An apparatus for controlling reaction which is accompanied by light emission, comprising:
a reaction apparatus for generating a light emitting body;
an optical guide for light from said light emitting body;
a spectroscope apparatus for separating light from said optical guide into spectral components, said spectroscope apparatus including a first spectroscope, a second spectroscope coupled with said first spectroscope through an intermediate slit, and drive means, said first spectroscope being made up of a collimator system and a light dispersing optical system, said light dispersing optical system including a light dispersing grating and a first optical system for leading the dispersed light from said light dispersing grating to said intermediate slit, said collimator system converting light rays from said optical guide into parallel rays incident on said light dispersing grating, said second spectroscope being made up of a light mixing optical system and an image formation optical system for forming an image of mixed light from said light mixing optical system, said light mixing optical system including a light mixing grating and a second optical system for focusing light from said intermediate slit on said light mixing grating, said drive means driving said light dispersing optical system and said light mixing optical system so that said light dispersing optical system and said light mixing optical system are optically symmetrical with respect to said intermediate slit;
a monitor for displaying an image, said image being formed of mixed light corresponding to that part of said spectral components which exists in one of different wavelength ranges;
a memory for storing a plurality of reference images; and
a controller for comparing a plurality of images corresponding to said wavelength ranges with the reference images read out of said memory, to control variable quantities concerning the state of said light emitting body so that at least one of said images agrees with a corresponding one of said reference images.

2. An apparatus for controlling reaction which is accompanied by light emission, as claimed in claim 1, wherein a light amplifying element is inserted into said image formation optical system of said spectroscope apparatus.

3. An apparatus for controlling reaction which is accompanied by light emission, as claimed in claim 1 or 2, wherein the width of said intermediate slit can be varied, and it is possible to vary the rotational angle of each of the light dispersing grating and the light mixing grating continuously so that the light dispersing grating and the light mixing grating are optically symmetrical with respect to said intermediate slit.

4. An apparatus for controlling reaction which is accompanied by light emission, as claimed in claim 3, wherein said optical guide is provided with a lens capable of transmitting ultraviolet rays and visible rays.

5. An apparatus for controlling reaction which is accompanied by light emission, as claimed in claim 4, further comprising an image processor for expressing the light intensity distribution at an image formed of mixed light, in colors.

* * * * *